United States Patent [19]

Susa et al.

[11] Patent Number: 4,825,868
[45] Date of Patent: May 2, 1989

[54] FAR INFRARED RAY RADIATING MATTRESS

[75] Inventors: Michitaro Susa; Tadao Sato, both of Tokyo, Japan

[73] Assignee: Tensho Electric Industrial Co., Ltd., Tokyo, Japan

[21] Appl. No.: 64,604

[22] Filed: Jun. 22, 1987

[51] Int. Cl.⁴ .................. A61N 33/06; A61F 7/00; A47L 21/04; H05B 1/00
[52] U.S. Cl. .................. 128/376; 128/399; 128/419 R; 5/421; 5/468; 219/217; 219/553; 273/DIG. 8
[58] Field of Search .............. 128/399, 376, 377, 378; 5/421, 448, 461, 468, 481; 219/217, 548, 553, 549

[56] References Cited

U.S. PATENT DOCUMENTS

| | | | |
|---|---|---|---|
| 811,094 | 1/1906 | Robertson | 128/376 |
| 4,047,254 | 9/1977 | Hamasu | 5/421 |
| 4,388,738 | 6/1983 | Wagner | 5/421 |
| 4,498,477 | 2/1985 | Masuda et al. | 5/468 |
| 4,680,822 | 7/1987 | Fujino et al. | 5/448 |
| 4,700,054 | 10/1987 | Triplett et al. | 219/553 |

FOREIGN PATENT DOCUMENTS

| | | | |
|---|---|---|---|
| 2916110 | 10/1980 | Fed. Rep. of Germany | 5/421 |
| 32846 | 3/1979 | Japan | 219/548 |
| 7503964 | 10/1975 | Netherlands | 128/419 N |

*Primary Examiner*—Richard C. Pinkham
*Assistant Examiner*—Mark S. Graham
*Attorney, Agent, or Firm*—Wenderoth, Lind & Ponack

[57] ABSTRACT

A far infrared ray radiating mattress has a three layer structure including a lower layer of plate-like resilient and foamed synthetic resin, a middle layer of foamed synthetic resin corrugated in a longitudinal direction and having a plurality of protrusions provided on the upper surface thereof; a sheet-like far infrared ray radiating heater is provided on the three layer structure; and a cover is provided so that the three layer structure and the sheet-like heater are surrounded thereby.

7 Claims, 4 Drawing Sheets

FAR INFRARED RAY RADIATING MATTRESS

BACKGROUND OF THE INVENTION

Infrared rays in the non-visual range having a long wave-length such as far infrared rays have an excellent thermal effect such as high absorption of heat rays into a human body, promotion of circulation of blood and recovery of fatigue of muscles. In the prior art, there has been used a mattress for radiating far infrared rays as shown in FIG. 6. The prior mattress comprises a relatively solid plate-like support A, a sheet-like heater B provided on the support a from the top to the bottom of the mattress and having electric resistance material of carbon in a rectagular form covered with an insulated sheet of vinyl, a thin cushion body C of chemical fiber or foamed polyurethane in the form of a plate provided on the heater B and an outer cover D covering a laminate of the support A, the heater B and the cushion body C.

However, since such a prior mattress radiating far infared rays has the sheet-like heater including the cover of vinyl, there is no ventilation of air and humidity and/or sweat is difficult to remove from the mattress. This causes the user to feel uncomfortable. Also after the mattress is used for a long time, the resilience of the cushion body decreases and humidity and/or sweat is more difficult to remove from the mattress. Thus, moisture remains in the mattress, which causes mildew and/or a bad odor to occur in the mattress. Furthermore, since the prior mattress is relatively thin and solid, the user feels and produces only thermal effects. In addition thereto, since the mattress is required to have large dimensions sufficient for covering the human body from the feet to the breast thereof, high electric power is required to be consumed.

SUMMARY OF THE INVENTION

Accordingly, it is a principal object of the invention to provide a mattress adapted to have a good ventilation of air so as to allow removal of humidity and/or sweat, which tend to be accumulated in the prior mattress and provide for the removal of mildew and/or a bad smell.

It is another object of the invention to provide a mattress adapted to radiate for infrared rays while the electric power is saved, which can avoid use of a large amount of electric power required for the prior mattress.

It is a further object of the invention to provide a mattress adapted to have a self-adjusting temperature without any temperature controller, and to effectively prevent fire from being caused and burns at low temperature from being caused.

It is a further object of the invention to provide a mattress adapted to provide a finger pressure effect to a human body on the mattress.

It is a further object of the invention to provide a mattress adapted to provide no feeling of rigid sleeping to a human body on the mattress.

In accordance with the invention, there is provided a far infrared ray radiating mattress comprising a three layer structure including a lower layer of plate-like resilient and foamed synthetic resin, a middle layer of foamed synthetic resin corrugated in a longitudinal direction and resistant to a compression load and an upper layer of foamed synthetic resin corrugated in a longitudinal direction and having a plurality of protrusions provided on the upper surface thereof; a far infrared ray radiation sheet-like heater provided on the three layer structure; and a cover provided so that the three layer structure and the sheet-like heater are surrounded thereby.

BRIEF DESCRIPTION OF THE DRAWINGS

The above and other objects and features of the invention will be apparent from the description of embodiments of the invention taken along with reference to the accompanying drawings in which.

DETAILED DESCRIPTION OF THE PREFERRED EMBODIMENTS

Figure 1:
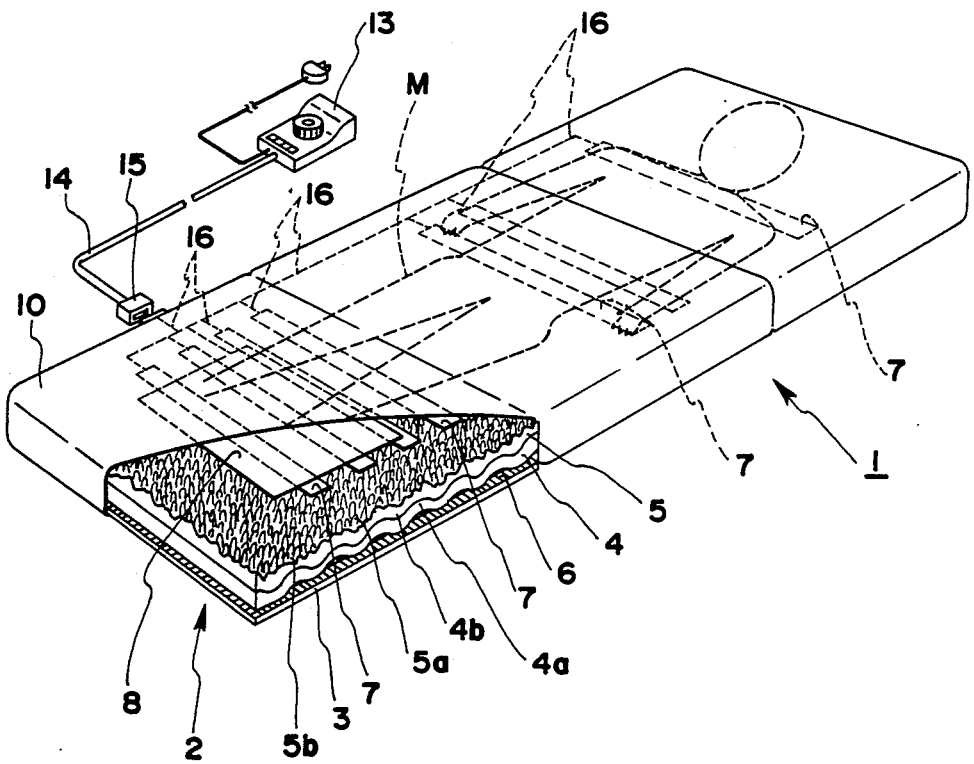
FIG. 1 is a perspective view of a far infrared ray radiating mattress constructed in accordance with one embodiment of the invention with a portion broken away for explanation thereof.

Referring now to FIG. 1, there is shown a far infrared ray radiating mattress 1 constructed in accordance with one embodiment of the invention. The mattrress 1 comprises a three layer structure 2 which includes a low layer of plate-like resilient and foamed synthetic resin such as foamed polyurethane which serves to absorb external vibration which might disturb the user's sleep, a middle layer 4 of foamed synthetic resin such as foamed polyethylene corrugated in a longitudinal direction so as to have transverse protrusions 4a and recesses 4b repeated in the longitudinal direction and having a resistance to a compression load, an upper layer 5 of foamed synthetic resin such as foamed polyurethane corrugated in a longitudinal direction and having a plurality of protrusions 5a provided on the upper surface thereof. The middle layer 4 is preferably a relatively rigid corrugated body which serves to positively support the weight of a human body M lying on the mattress 1 in a sleeping position without the weighty hip and back of the human body sinking excessively into the mattress. It will be noted that this serves to remove distortion of the back bone which tends to be generated due to unnatural posture during daytime. The upper layer 5 serves to softly support the human body on the middle layer 4 (particularly on the protrusions 4a). It should be noted that the protrusions 5a serve to provide a finger pressure effect on the human body because the protrusions 5a pressurize the skin surfaces of the human body. The three layer structure 2 preferably includes a net body 6 disposed between the lower layer 3 and the middle layer 4 to support the weight of the human body so as to make the use of the mattress stable for a longer time.

Figure 3:
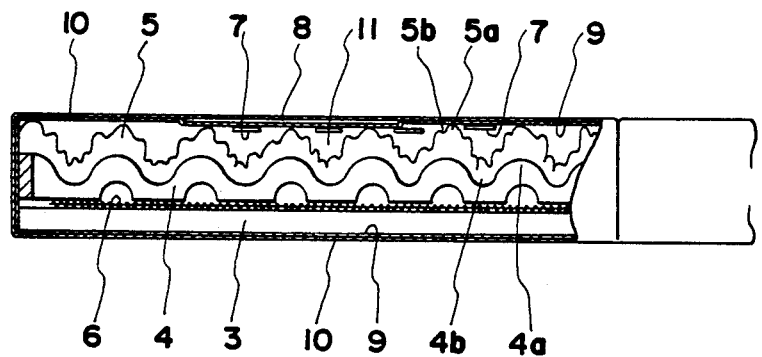
FIG. 3 is a longitudinal cross sectional view of the mattress shown in FIG. 1.

A sheet-like far infrared ray radiating heater 7 is provided on the three layer structure 2. In the illustrated embodiment, the heater 7 may be formed of a plurality of heating sheets in the form of spaced strips in a manner as shown in FIGS. 1 and 3 with the longitudinal direction arranged in the direction of the width of the mattress 1 and with the strips positioned corresponding to the recesses of the corrugations of the three layer structure 2 so that they are disposed in a manner facing the feet, hips and shoulders of the human boey. Thus, it will be noted that the feet, hips and shoulders of the human body which tend to become most fatigues have the effects of far infrared ray radiation and of being heated.

Furthermore, with the sheet-like heater 7 disposed corresponding to the recesses of the corrugation of the three layer structure 2, the heater 7 has no pressure from the human body M applied thereto with the result that the heater 7 is never damaged even though it is used for a long time, which causes it to have a longer life. Also, the heater has no close engagement with the skin of the human body M and a space 11 in formed between the heater 7 of the three layer structure 2 at the recesses of the corrugation thereof, which allows air to have good circulate therethrough.

Figure 2:
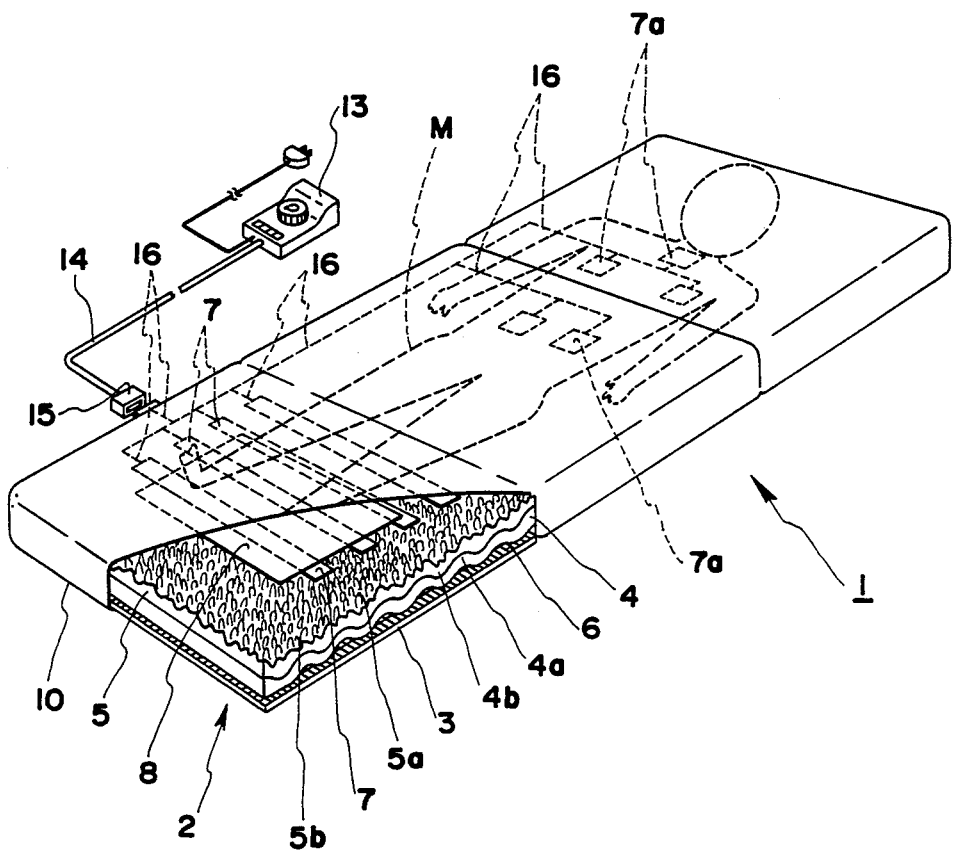
FIG. 2 is a perspective view of a far infrared ray radiating mattress constructed in accordance with another embodiment of the invention with a portion broken away for explanation thereof.

Radiation of heat into a body is effectively accomplished by the mattress constructed in accordance with another embodiment shown in FIG. 2. As shown in this figure, a far infrared ray radiating sheet-like heater 7a over the three layer structure 2 can be preferably formed of many pieces in rectangular or round form disposed corresponding to the important regions of the human body M at the back thereof. Furthermore, the pieces of the heater 7a have a smaller area than the strips in FIG. 1 with the result that they contact the human body M over a smaller area, which prevents humidity and sweat tending to be accumulated in the mattress from increasing and which permits air to have good passage through the mattress. This allows the mattress to be used without any feeling of discomfort.

In the embodiment of FIG. 2, a portion of the heater 7 corresponding to the feet of the human body M may be formed of sheets in the form of strips. This allows the feet of the human body M to be effectively heated during winter.

Figure 4:
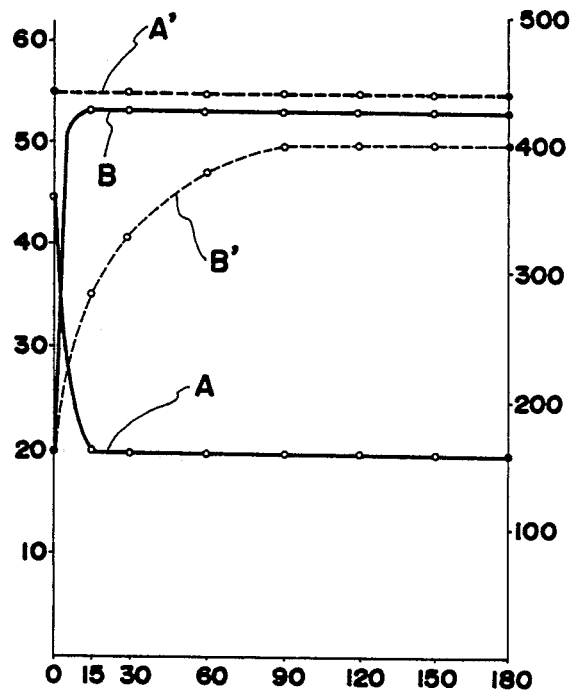
FIG. 4 illustrates curves of temperature characteristics of various far infrared ray radiating sheet-like heaters.

The sheet-like heater 7 or 7a may be formed of an electric resistance body such as commercially available carbon particles coated with a far infrared ray radiation coating layer and further coated with an insulating sheet of material such as synthetic resin. Alternatively, it may be formed of organic material such as a combination of fine particles of graphite and high polymer which has a property of self-adjustment of temperature. This allows the electric resistance and the current therethrough to decrease as the temperature of the heater rises so as to maintain the heater at a constant temperature. FIG. 4 illustrates the consumption of electric power of various heaters. In FIG. 4, lines A and A' show the characteristic of temperature of the heater having no self-adjustment of temperature and the consumption of electric power thereof while lines B and B' show those of the heater having a self-adjustment of temperature. As noted from FIG. 4, the heater having the self-adjustment of temperature has the temperature automatically maintained at a constant value and has less than 50% of the consumption of electric power (Watt) of the heater having no self-adjustment of temperature. Thus, it will be noted that the mattress including the heater having the self-adjustment of temperature is not required to be provided with a temperature adjuster or switch for preventing the temperature from excessively rising and that electric energy can be effectively saved.

It should be noted that radiation of far infrared rays should be effectively made toward the human body in an upward direction. This is effectively accomplished by providing the far infrared ray radiation member 7B of aluminium foil or aluminium clad resin sheet at the back of the heating member 7A. This serves to more effectively save electric power.

An ion bed strip 8 flexible woven fiber coated with a good conductor including carbon may be provided on the heater 7 in the mattrress 1 in the area of the feet of the human body M. A minus ion source of high voltage not shown supplies minus ions to the ion bed strip 8 to prevent the human body from being oxidized.

To the sheet-like heater 7 or 7a and the ion bed strip 8 is supplied a controlled amount of electric power from a control 13 through a connection cord 14, a connector 15 and a connection cord 16. In the embodiment of FIG. 2, a turn-over switch not shown may be provided to enable only the sheet-like heater 7a to be operated. This allows the application of the rays to limited regions of the human body by radiation of far infrared rays.

The sheet-like heater 7 or 7a and the ion bed strip 8 may be secured to the three layer structure 2 by means of adhesives or any means such as cords or clasps. Alternatively, the ion bed strip 8 may be disposed between a wrapper 9 of woven fiber of nonwoven fiber for air ventilation and an outer cover 190 provided on the wrapper 9 while the sheet-like heater 7 or 7a may be attached to the wrapper 9 by adhesives or sewing. Otherwise, the sheet-like heater 7a may be provided by being contained in bags which are in turn secured to the wrapped 9 by any suitable means.

Although the mattress of the invention may be integrally formed when it is to be used on a bed, it may be foldable in two or three when it is used in Japanese rooms so as to be convenient for containing and transporting it.

When the mattress of the invention is to be used, the control 13 is connected to the sheet-like heater 7 by inserting the connector 15 into a plug not shown and is connected to the power source by means of a power source switch. In this manner, the far infrared rays are radiated from the sheet-like heater to the human body M on the mattress 10 to heat the human body M and at the same time minus ions pass from the ion bed strip 8 through the human body M. The protrusions 5a on the upper layer 5 of the three layer structure 2 serve to support the human body M.

It should be also noted that the mattress 1 has a good air ventilation because of the smaller area of the sheet-like heater 7 or 7a as compared to the prior art heater and the corrugated middle and upper layers 4 and 5 of the three layer structure 2. This allows removal of humidity and/or sweat, which tend to be accumulated in the mattress and provides for the removal of mildew and/or a bed smell.

Figure 5:
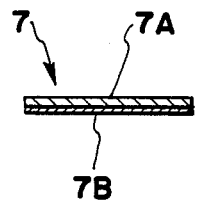
FIG. 5 is a cross sectional view of a far infrared ray radiating heater used for the invention.
Figure 6:
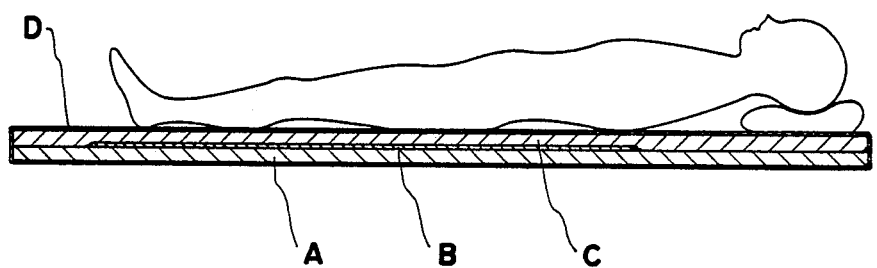
FIG. 6 is a cross sectional view of a prior art far infared ray radiating mattress.

Furthermore, it will be noted that the far infrared rays can be radiated while the electric power is saved, which avoids the high electric power required for the prior mattress of FIG. 6. As aforementioned, the sheet-like heater having the self-adjustment of temperature does not require any temperature controller, is unlikely to cause fire and/or burns at low temperature and enables the electric power to be saved. With the far infared ray radiating member 7B disposed under the heater member 7A as shown in FIG. 5, even more electric power can be saved. Also, with the sheet-like heater 7 provided on the wrapper 9, the three layer structure 2 is separately provided from the sheet-like heater 7 with the result that the mattress can be more easily manufactured, conserved and checied because it can be easily assembled and disassembled.

In addition thereto, since the mattress comprises the three layer structure particularly constructed in accordance with the invention, the finger pressure support can be provided to the human body M by the upper layer 5 and a cushion can be provided to the human body M because of dispersion of the pressure from the human body M. It will be noted that the middle layer 4 of the three layer structure 2 prevents the hip and back of the human body M from sinking so as to support the weight of the human body M with proper rigidness so as to provide a proper sleeping posture thereto and to prevent external vibrations through the lower layer 3 from being transferred to the mattress 1. Thus, it will be noted that the mattress 1 of the invention never provides the feeling of rigid sleeping to the human body M.

While some embodiments of the invention have been illustrated and described with reference to the accompanying drawings, it will be understood by those skilled in the art that they are by way of example, and that various changes and modifications may be made without departing from the spirit and scope of the invention, which is intended to be defined only to the appended claims.

What is claimed is:

1. A far infrared ray radiation mattress comprising:
   a three layer structure including a lower layer of plate-like resilient and foamed synthetic resin, a middle layer of foamed synthetic resin corrugated in the direction of the length of the mattress and having corrugations extending transversely thereof and resistant to a compression load, and an upper layer of foamed synthetic resin conforming to the corrugations of said middle layer and having a plurality of protrusions provided on the upper surface thereof;
   a cover around said three layer structure and leaving spaces between the under surface of said cover and the recesses between corrugations in said upper layer; and
   a plurality of far infrared ray radiation sheet-like heater elements disposed on the under side of said cover over said upper layer at at least some of said recesses and facing said recesses.

2. A far infrared ray radiation mattress as claimed in claim 1, wherein said sheet-like heater elements are a plurality of strips extending parallel to said recesses.

3. A far infrared ray radiating mattress as claimed in claim 1 wherein said sheet-like heater elements comprise a plurality of elongated strips disposed extending parallel to said some of said recesses and a plurality of short strips disposed opposed to others of said recesses.

4. a far infrared ray radiating mattress as claimed in claim 3 wherein said elements are at areas on said mattress on which important regions of a sleeper will usually rest.

5. A far infrared ray radiating mattress as claimed in claim 1, wherein said cover is a flexible and ventilative material.

6. A far infrared ray radiating mattress as claimed in claim 1, wherein said sheet-like heater elements are each formed of material which is a combination of fine carbon particles and a high polymer material so as to be self-adjusting with respect to temperature.

7. A far infrared ray radiating mattress as claimed in claim 1, wherein said sheet-like heater elements are each constituted by a far infrared ray radiating member and an electric resistance heating member against the upper surface thereof.

* * * * *